United States Patent [19]

Heinze et al.

[11] Patent Number: 4,805,621
[45] Date of Patent: Feb. 21, 1989

[54] APPARATUS FOR MEASURING IMPEDANCE OF BODY TISSUE

[75] Inventors: Roland Heinze; Karl Stangl, both of Munich, Fed. Rep. of Germany

[73] Assignee: Siemens Aktiengesellschaft, Berlin and Munich, Fed. Rep. of Germany

[21] Appl. No.: 61,549

[22] Filed: Jun. 15, 1987

[30] Foreign Application Priority Data

Jun. 16, 1986 [DE] Fed. Rep. of Germany ....... 3620280

[51] Int. Cl.$^4$ ...................... A61N 1/00; H05G 00/00
[52] U.S. Cl. ............................. 128/419 PG; 128/734
[58] Field of Search ................ 128/419 PG, 720, 723, 128/734

[56] References Cited

U.S. PATENT DOCUMENTS

| | | | |
|---|---|---|---|
| 3,532,086 | 10/1987 | Underwood et al. | 128/668 |
| 4,030,485 | 6/1977 | Warner | 128/667 |
| 4,303,075 | 12/1982 | Heilman et al. | 128/419 PG |
| 4,535,774 | 8/1985 | Olson | 128/419 PG |
| 4,552,150 | 11/1985 | Zacouto | 128/419 PG |
| 4,596,251 | 6/1986 | Plicchi et al. | 128/419 PG |
| 4,674,518 | 6/1987 | Salo | 128/419 PG |
| 4,694,830 | 9/1987 | Lekholm | 128/419 PG |
| 4,702,253 | 10/1987 | Nappholz et al. | 128/419 PG |

FOREIGN PATENT DOCUMENTS

| | | | |
|---|---|---|---|
| 0089014 | 5/1984 | European Pat. Off. | 128/419 PG |
| 2070282 | 2/1980 | United Kingdom | 128/419 PG |

OTHER PUBLICATIONS

"Methods of filtering the heart-beat artefact from the breathing waveform of infants by impedance pneumography", Wilson et al, Medical & Biological Engineering & Computing, vol. 20, No. 3, May 1982, pp. 293-298.

Primary Examiner—Francis Jaworski
Assistant Examiner—George Manuel

[57] ABSTRACT

An apparatus for measuring the impedance of body tissue has a signal source connected to the tissue to be measured which supplies an electrical signal to the tissue, a unit for acquiring an impedance signal from the body tissue dependent on the electrical signal, and an evaluation stage for the impedance signal. The evaluation stage filters out low frequency signal components corresponding to the conductance of the tissue, and has a signal output to which the signal components which were filtered out are supplied.

16 Claims, 1 Drawing Sheet

APPARATUS FOR MEASURING IMPEDANCE OF BODY TISSUE

BACKGROUND OF THE INVENTION

1. Related Application

The present application is related to a co-pending application of the same inventors entitled "Apparatus For Measuring Impedance Of Body Tissue" filed simultaneously herewith, Ser. No. 061,547.

2. Field of the Invention

The present invention is directed to an apparatus for making an impedance measurement of body tissue, and in particular to such an apparatus having a signal source which impresses a signal on the tissue to be measured, and means for acquiring an impedance signal from the tissue dependent on the impresses signal.

3. Description of the Prior Art

Body tissue impedance measurement devices are known wherein an impedance signal is obtained from body tissue to which a current or voltage signal has been supplied. Such known devices include an evaluation means which separates higher frequency signal components from the impedance signal so acquired. Such a unit is described, for example, in combination with frequency-controlled heart pacemakers in U.S. Pat. No. 4,303,705.

Other devices of this type are known wherein the evaluation means separates both lower frequency and higher frequency signal components from the impedance signal to identify the degree of blood loss occurring during an operation, as in U.S. Pat. No. 3,532,086. The low-frequency component is a measure of the blood volume.

Heretofore, impedance measurements in body tissue (including blood) were for the purpose of identifying mechanical volume changes of the body, for example, the volume of a beating heart or the thorax volume during respiration movement. The change in the impedance can then be employed for controlling the stimulation pulse frequency of a heart pacemaker. In simplified terms, the basis of making such an impedance measurement is the following physical relationship:

$$R = l / (\sigma_R \cdot F)$$

wherein R is the impedance, $\sigma_R$ is the conductance (1/Ω·cm), l is the effective electrode spacing (cm), and F is the effective line cross-section (cm$^2$) between the electrodes.

Thus by measuring the periodic impedance fluctuation, the changes in l or F of the line path are monitored.

Thus in such known devices, a direct measurement of the metabolism of interest, which in turn is a direct measure of certain types of body stress or body changes, is not possible.

SUMMARY OF THE INVENTION

It is an object of the present invention to provide an apparatus for making an impedance measurement of body tissue which enables a signal directly corresponding to the metabolism of interest to be generated.

The above object is achieved in accordance with the principles of the present invention in an apparatus for impedance measurement having an evaluation means which filters out the low frequency signal components of the impedance signal, those low frequency components corresponding to the conductance, and the components which are filtered out are supplied to a signal output.

The invention is based on the perception that metabolic components are associated with the conductance $\sigma_R$ in the aforementioned relationship. These components specify a direct measure for the metabolism, and thus constitute a direct relationship to the body stress. The invention also proceeds based on the perception that higher-frequency signal components are contained within the required impedance signal, which reflect changes in l or F, and that a lower frequency component is also present which is a direct measure for the conductance $\sigma_R$. This is in contrast to the known methods of, for example, U.S. Pat. No. 3,532,086, which uses the low-frequency components as indicators for blood volume. As stated above, known devices for impedance measurement in heart pacemaker technology such as, for example, the impedance measuring device in U.S. Pat. No. 4,303,075, filter the higher frequency signal components out of the acquired impedance signal as a measure for the respiration or the beat volume of the heart and thus control, for example, the frequency of the pacemaker. In the apparatus disclosed and claimed herein, however, the lower frequency signal components of the impedance signal are filtered out instead of the higher frequency signal components. A signal which is directly dependent on the conductance is thus obtained, permitting a direct statement (signal) identifying the patient's metabolism to be made, which in turn is a direct indicator of the momentary stress of the patient. In the context of a frequency-controlled heart pacemaker, this signal is a considerably more precise control signal for the stimulation frequency than the conventionally used higher-frequency component of the impedance signal.

In one embodiment of the invention, the low-frequency components of the measured impedance signal can be supplied as a control signal to the frequency control unit of a heart pacemaker for controlling the stimulation frequency. This is accomplished by modifying the stimulation frequency in accord with the changing conductivity, as measured by the device.

In another embodiment of the invention, the limit frequency of the low-pass filter, which is used to filter out the lower frequency components, may be variable dependent on the stimulation frequency. The limit frequency in this embodiment is shifted upwardly (toward higher frequency values) given an increasing stimulation frequency, and is correspondingly shifted downwardly (toward lower frequency values) given decreasing stimulation frequency. Such variation in the limit frequency has the advantage of maintaining the limit frequency of the filter optimally high dependent on the respiratory frequency, which changes dependent on the stress to the patient (analogously to the changing stimulation frequency), but nonetheless will be maintained below the respiratory frequency. A disturbing influence of the respiration on the measured result thus cannot occur.

In a further embodiment of the invention, a means for compensating for the influence of temperature is additionally divided, so that the measured conductance is rid of temperature influences.

DESCRIPTION OF THE PREFERRED EMBODIMENTS

Figure 1:
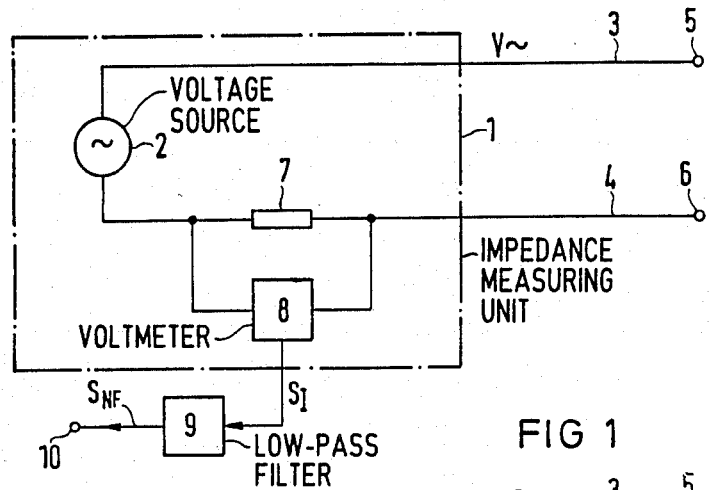
FIG. 1 is a schematic block diagram of a portion of an impedance measuring device constructed in accordance with the principles of the present invention.

An impedance measuring unit 1 constructed in accordance with the principles of the present invention is shown in FIG. 1. The impedance measuring unit includes a signal source for impressing an electrical signal on the tissue of a patient. In the embodiment of FIG. 1, the signal source is an alternating voltage source 2 (for example, a 1 kHz ac voltage generator) which impresses an ac voltage V∼ of unchanging amplitude (for example, 1 kHz ac voltage) on body tissue (not shown) via electrode lines 3 and 4, with associated electrodes 5 and 6. The apparatus shown in FIG. 1 is preferably for intracorporeal measurement. At least the electrodes 5 and 6 are thus implanted in the body tissue, preferably the entire measuring instrument is implanted. Dependent on the impressed ac voltage V∼, the voltage drop caused by the current in the electrode lines 3 and 4 is acquired via a low-impedance series resistor 7 (for example, 100 ohms), by means of a voltmeter 8. The output signal of the voltmeter 8 is supplied to a low-pass filter 9 having an upper limit frequency in the range from about 0.1 through about 0.4 Hz (the upper limit frequency being preferably variable in this frequency range, as described in detail below with reference to FIG. 3). The low-pass filter 9 filters only the low-frequency signal components $S_{NF}$ out of the output signal $S_I$ (impedance signal) from the voltmeter 8. The low-frequency signal components $S_{NF}$ correspond to the conductance $\sigma_R$ in the body tissue. The low-frequency signal components $S_{NF}$ filtered out are supplied to a signal output 10 of the low-pass filter 9.

Figure 2:
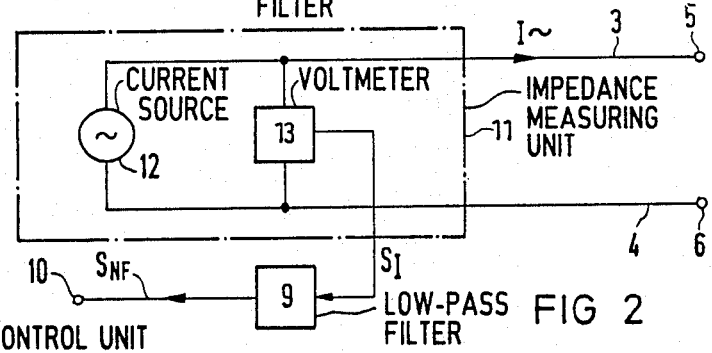
FIG. 2 is a schematic block diagram of an impedance measuring device constructed in accordance with the principles of the present invention.

In the embodiment of FIG. 2, another embodiment of an impedance measuring unit 11 is shown which includes an alternating current source 12 (for example, a 1 kHz alternating current source) which impresses an alternating current I∼ of unchanging amplitude (for example, 1 kHz alternating current) on the body tissue via the electrode lines 3 and 4 and the associated electrodes 5 and 6. The entire measuring system is again preferably designed as an intracorporeal measuring system. In this embodiment, the ac voltage between the electrodes 5 and 6 is measured by a parallel voltmeter 13 which contains a divider for forming the value 1/V∼. The output signal $S_I$ (impedance signal) of the voltmeter 13 is then evaluated in the low-pass filter 9 in the same manner as set forth above in connection with FIG. 1.

Figure 3:
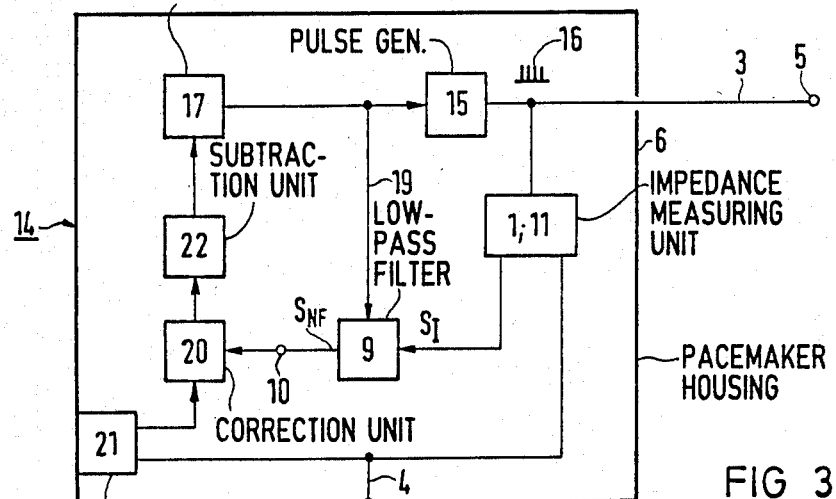
FIG. 3 is a schematic block diagram showing the embodiment of an impedance measuring device of the type shown in either FIG. 1 or FIG. 2 in a frequency-controlled heart pacemaker.

A heart pacemaker 14 embodying either of the embodiments of FIG. 1 or FIG. 2 is shown in FIG. 3. The pacemaker 14 is a frequency-controlled heart pacemaker. Identical components identified above are provided with the same reference numerals in FIG. 3. The electrode 5 in the embodiment of FIG. 3 serves simultaneously as the stimulation electrode for the heart pacemaker 14, whereas the electrode 6 is formed by the conductive (for example, metallic) housing of the heart pacemaker 14. The electrode line 3 corresponds to the stimulation catheter of the heart pacemaker 14.

The frequency-controlled heart pacemaker 14 includes a pulse generator 15 for generating stimulation pulses schematically identified at 16. The repetition rate of the stimulation pulses 16 (stimulation frequency) is controllable at the pulse generator 15 by a frequency control unit 17. The stimulation frequency is controllable dependent on the filtered-out, low-frequency signal component $S_{NF}$ at the output 10 of the low-pass filter 9. Control is undertaken by modifying the stimulation frequency in proportion to the changing conductance $\sigma_R$. The stimulation frequency thus increases when the low-frequency signal component $S_{NF}$ filtered out (and thus, the conductance $\sigma_R$) increases. Conversely, the stimulation frequency is lowered when the signal component $S_{NF}$ (and, thus, the conductance $\sigma_R$) decreases.

As shown in FIG. 3, the limit frequency of the low-pass filter 9 is adjustable via a control line 19, dependent on the output signal of the frequency control unit 17. Control of the limit frequency is undertaken such that the limit frequency is shifted toward higher frequency values in the range of about 0.1 through about 0.4 Hz given an increasing stimulation frequency, and is correspondingly shifted toward lower frequency values in that range given a decreasing stimulation frequency. As discussed above, this results in the advantage that the measured result remains uninfluenced by the respiration of the patient, while maintaining the limit frequency of the low-pass filter 9 at the desired highest possible value.

As also shown in FIG. 3, the stimulation frequency can be controlled by the frequency control unit 17 through a correction element 20 which compensates for temperature influences, rather than being controlled directly by the signal $S_{NF}$. The conductance $\sigma_R$ increases with increasing temperature. The correction unit 20 corrects the signal $S_{NF}$ for the conductance inverse fashion. A temperature sensor 21 acquires the temperature value, the temperature sensor 21 being disposed, for example, in the housing of the heart pacemaker or outside of the housing. The impedance measuring unit 1 or 11 and the low-pass filter 9 are preferably accommodated inside the pacemaker housing.

Instead of the temperature sensor 21 and the correction element 20, the stimulation catheter 3 may itself consist of a material (for example, NTC resistor material) which compensates for the temperature response of the conductivity. Another alternative is to integrate a resistor constructed of NTC material within the stimulation catheter 3.

The frequency control unit 17 may be connected to a subtraction stage 22 which subtracts a programmable fixed value (for example, between 80 and 90 percent of the mean value of the low-frequency signal) from the temperature-compensated low-frequency signal $S_{NF}$. An offset signal component which is not needed for frequency control may be thereby eliminated.

Although modifications and changes may be suggested by those skilled in the art it is the intention of the inventors to embody within the patent warranted hereon all changes and modifications as reasonably and properly come within the scope of their contribution to the art.

We claim as our invention:

1. An apparatus for metabolism measurement of body tissue, said body tissue having a conductance, said apparatus comprising:
   a signal source adapted to be connected to said body tissue for impressing an electrical signal into said body tissue;
   means adapted to be connected to said body tissue for acquiring an impedance signal therefrom dependent on the impressed electrical signal and said conductance, said impedance signal including higher-frequency signal components corresponding to periodic body cycles and lower-frequency signal components corresponding to the metabolism of said body tissue; and
   an evaluation means connected to said means for acquiring said impedance signal for evaluating only said signal components in said impedance signal corresponding to the metabolism of said body tissue for making a metabolism measurement, said evaluation means including means for filtering said lower-frequency signal components out of said impedance signal, said means for filtering having a signal output to which the filtered-out signal components are supplied.

2. An apparatus as claimed in claim 1, wherein said means for filtering is a low-pass filter having an upper limit frequency which permits said lower-frequency signal components of said impedance signal to pass.

3. An apparatus as claimed in claim 2, wherein said low-pass filter has an upper limit frequency in the range of from about 0.1 through about 0.4 Hz.

4. An apparatus as claimed in claim 2, further comprising means for varying said limit frequency of said low-pass filter.

5. An apparatus as claimed in claim 1, further comprising:
   means for supplying stimulation pulses at a controllable frequency to a patient in whom said body tissue is disposed; and
   means for controlling the pulse frequency of said means for supplying stimulation pulses, said means for controlling having an input connected to said means for filtering, and including means for modifying said stimulation frequency corresponding to changes in said body tissue metabolism based on said signal components passed by said means for filtering.

6. An apparatus as claimed in claim 5, wherein said means for filtering is a low-pass filter having a limit frequency and further comprising means for varying said limit frequency dependent on said stimulation frequency for shifting said limit frequency toward higher frequency values given increasing stimulation frequency and shifting said limit frequency toward lower frequency values given decreasing stimulation frequency.

7. An apparatus as claimed in claim 5, further comprising:
   means for compensating for the influence of temperature on said lower frequency signal components; and
   a subtraction means connected between said means for compensating and said means for controlling the stimulation frequency, said subtraction means subtracting a programmable fixed value from an output of said means for compensating.

8. An apparatus as claimed in claim 7, wherein said subtraction means includes means for calculating mean value of said lower frequency signal components, and means for subtracting a programmable value in the region of from about 80 through about 90% of said mean value.

9. An apparatus as claimed in claim 1, further comprising means for compensating for the influence of temperature on said lower-frequency signal components.

10. A method for metabolism measurement of body tissue, said body tissue having a conductance, said method comprising the steps of:
    impressing an electrical signal in said body tissue;
    acquiring an impedance signal from said body tissue dependent on the impressed electrical signal and said conductance, said impedance signal having higher-frequency signal components corresponding to periodic body cycles and lower-frequency signal components corresponding to the metabolism of said body tissue;
    filtering out the lower-frequency signal components of said impedance signal corresponding to said metabolism of said body tissue; and
    supplying only the lower-frequency signal components filtered out of said impedance signal to an output as a measure of the metabolism of said body tissue.

11. A method as claimed in claim 10 further comprising the steps of:
    stimulating the heart of a patient, in whom said body tissue is disposed, with stimulation pulses at a controllable frequency; and
    controlling the frequency of said stimulation pulses based on said lower-frequency signal components corresponding to said metabolism of said body tissue.

12. A method as claimed in claim 11, wherein the step of filtering is undertaken in a low-pass filter having a limit frequency, and comprising the additional step of:
    varying said limit frequency of said low pass filter dependent on said stimulation frequency.

13. A method as claimed in claim 12, wherein the step of varying is further defined by the steps of:
    shifting said limit frequency toward higher frequency values given increasing stimulation frequency; and
    shifting said limit frequency toward lower frequency values given decreasing stimulation frequency.

14. A method as claimed in claim 10, comprising the additional step of:
    compensating for the influence of temperature on said lower-frequency signal components.

15. A method as claimed in claim 14, comprising the additional step of:
    subtracting a programmable fixed value from said lower-frequency signal components after compensating for the influence of temperature.

16. A heart pacemaker for stimulating the heart of a patient in whom said pacemaker is implanted, said pacemaker comprising:
    a signal source means adapted to be connected to body tissue having a conductance in said patient for impressing an electrical measurement signal into said body tissue;
    means adapted to be connected to said body tissue for acquiring an impedance signal therefrom dependent on the impressed electrical measurement signal and said conductance, said impedance signal including higher-frequency signal components corresponding to periodic body cycles and lower-frequency signal components corresponding to said metabolism of said body tissue;

an evaluation means connected to said means for acquiring said impedance signal for evaluating said impedance signal, said evaluation means including means for filtering said lower-frequency signal components out of said impedance signal, said means for filtering having a signal output to which only the filtered-out signal components are supplied;

means for generating and supplying stimulation pulses to said heart of said patient at a variable frequency; and control means for said means for generating and supplying for varying said stimulation frequency at least partially in dependence on said filtered-out signal components at said signal output of said evaluation means.

* * * * *